United States Patent [19]

Lannelongue

[11] Patent Number: 4,919,669
[45] Date of Patent: Apr. 24, 1990

[54] SHOULDER PROSTHESIS

[76] Inventor: Jean Lannelongue, 2, rue Ferdinand Dubreuil, 37000 Tours, France

[21] Appl. No.: 153,384
[22] Filed: Feb. 8, 1988

[30] Foreign Application Priority Data

Feb. 9, 1987 [FR] France .................. 87 01524

[51] Int. Cl.⁵ ............................ A61F 2/40; A61F 2/30
[52] U.S. Cl. ........................................ 623/19; 623/18
[58] Field of Search ............................. 623/19, 18, 21

[56] References Cited

U.S. PATENT DOCUMENTS

| | | | |
|---|---|---|---|
| 3,803,641 | 4/1974 | Golyakhovsky | 623/19 |
| 3,916,451 | 11/1975 | Buechel et al. | 3/1.91 |
| 3,978,528 | 9/1976 | Crep | 3/1.91 |
| 4,045,826 | 9/1977 | Stroot | 3/1.91 |
| 4,106,130 | 8/1978 | Scales | 3/1.91 |
| 4,304,011 | 12/1981 | Whelan, III | 623/21 |
| 4,352,212 | 10/1982 | Greene, et al. | 623/21 |
| 4,524,467 | 6/1985 | De Carlo, Jr. | 623/19 |
| 4,549,319 | 10/1985 | Meyer | 623/22 |
| 4,550,450 | 11/1985 | Kinnett | 623/18 |
| 4,693,723 | 9/1987 | Gabard | 623/19 |

FOREIGN PATENT DOCUMENTS

| | | |
|---|---|---|
| 0149527 | 7/1985 | European Pat. Off. . |
| 3216111 | 10/1983 | Fed. Rep. of Germany . |
| 2541890 | 9/1984 | France . |
| 0127503 | 12/1984 | France . |
| 543881 | 12/1973 | Switzerland . |
| 2162753A | 2/1986 | United Kingdom . |

OTHER PUBLICATIONS

Zimmer Product Publication, Jun., 1978.

Primary Examiner—Richard J. Apley
Assistant Examiner—Stephanie L. Iantorno
Attorney, Agent, or Firm—Armstrong, Nikaido, Marmelstein, Kubovcik & Murray

[57] ABSTRACT

A shoulder prosthesis, of the type comprising a humeral piece intended to be fixed in a humerus to replace at least the head thereof and comprising a hollow tubular element which must be fixed in the humerus substantially along the longitudinal axis thereof and a cylindrical rod, the upper end of which carries a ball cooperating with a glenoid bearing surface to form the shoulder joint and the lower end of which is disposed in said tubular element, this and the rod being able to slide relative to each other, the glenoid bearing surface consisting of a glenoid piece which comprises an anchoring element intended to be inserted into a cavity formed in the scapula and a female hemispherical element, this latter cooperating with the male ball of the humeral piece.

18 Claims, 3 Drawing Sheets

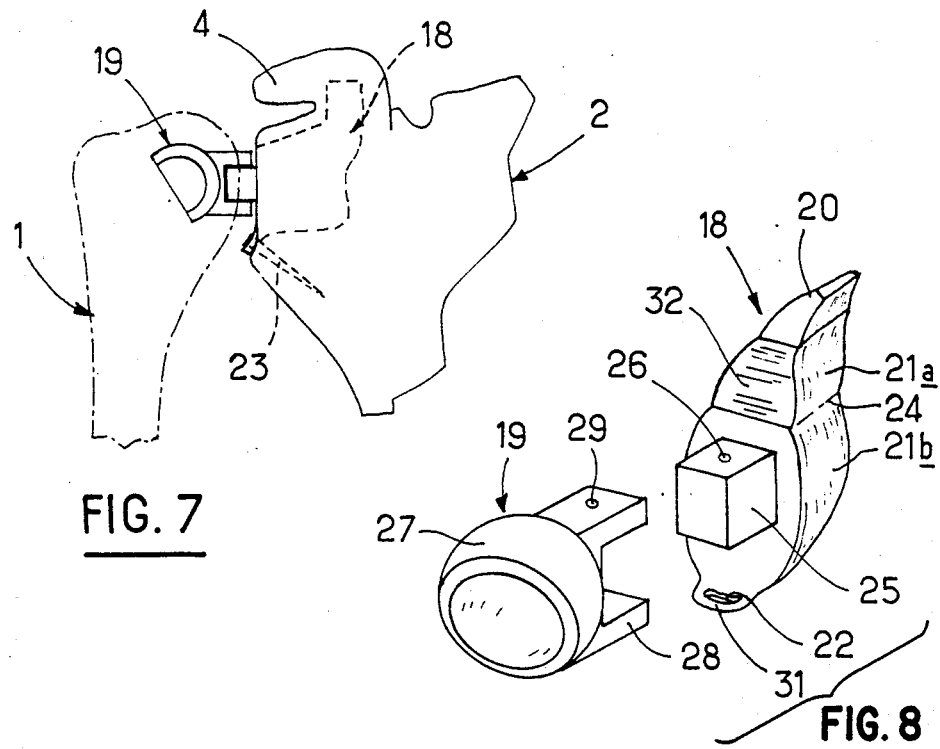
FIG. 7
FIG. 8
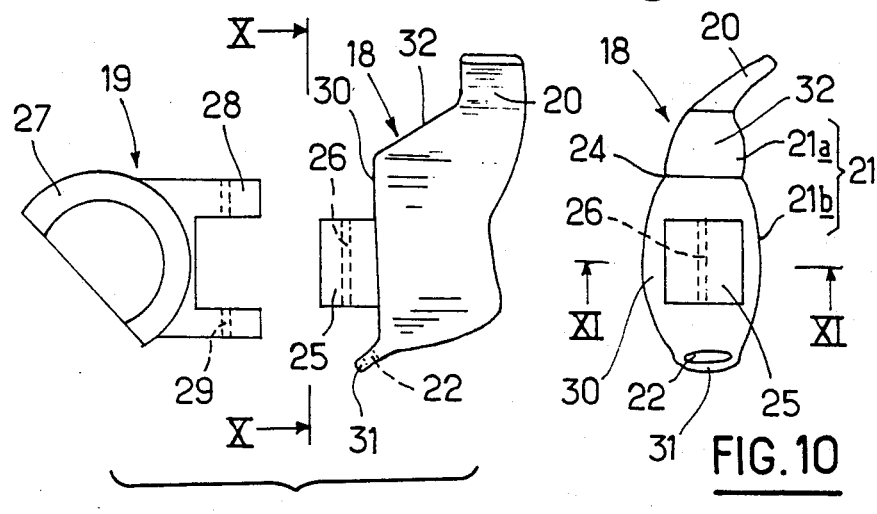
FIG. 9
FIG. 10

SHOULDER PROSTHESIS

BACKGROUND OF THE INVENTION

The present invention relates to a shoulder prosthesis, of the type comprising a humeral piece intended to be fixed in a humerus to replace at least the head thereof and comprising a hollow tubular element which must be fixed in the humerus substantially along the longitudinal axis thereof and a cylindrical rod, the upper end of which carries a ball cooperating with a glenoid bearing surface to form the shoulder joint and the lower end of which is disposed in said tubular element, this and the rod being able to slide relative to each other, the glenoid bearing surface consisting of a glenoid piece which comprises an anchoring element intended to be inserted into a cavity formed in the scapula and a female hemispherical element, this latter cooperating with the male ball of the humeral piece.

The humeral piece must be fixed in the upper end of the humerus to replace the head and if necessary the greater tuberosity thereof; the glenoid piece, occasionally referred to as the scapular piece, must be introduced into the scapula to replace the glenoid cavity thereof.

As is the case for any joint prosthesis, the fixation of each piece of this prosthesis in the bones poses a major problem. In fact, such fixation will always be of limited strength, because there cannot be total microscopic union between the living bone tissue and the inert material of the prosthesis. At present, there are two possibilities of improving such fixation: either to use prosthesis of rough surface such that the bone generates bony tissue which molds to the different uneven areas; or to use a plastic substance, which penetrates into the anfractuosities of the bone and thus renders the piece integral with the bone, such as, for example, methyl methacrylate.

Despite the use of one or other of these possibilities, the bone/prosthesis junction still remains a zone of weakness. However, it is indispensable that this junction be as strong as possible in order to permit the movements of the joint and to prevent the pains which are caused in the case of poor fixation. Moreover, working loose between the prosthesis and the bone causes destruction of the bone and consequently leads to detachment of the prosthesis.

In the case of a shoulder prosthesis, consisting of a humeral piece and a glenoid piece, the glenoid piece is that which is most susceptible to being separated from the scapula; in fact, this bone is of very slight thickness, approximately 1 cm, and of small surface area, approximately 4 to 6 cm$^2$. Moreover, the glenoid piece is subjected to upward thrusts caused by the muscles and the supports of the hand, and to downward tensions caused by the weight of the arm itself as well as by objects held in the hand. In the normal state, there exists a muscle group which is located between the acromion, a process of the scapula, and the head of the humerus, and which acts as a buffer and opposes the movement generating an upward pressure. Unfortunately, this muscle group wears out, and it is precisely when this group has worn out that it becomes necessary to contemplate the installation of a prosthesis, which therefore cannot use this group to prevent the upward movements.

One of the objects of the present invention is to provide a shoulder prosthesis comprising a humeral piece and if necessary a glenoid piece, of the type defined in the foregoing, the fixation of which in the scapula is of longer duration.

Another object of the present invention is to provide such a prosthesis which is stable, i.e., such that the pieces thereof are not susceptible to becoming displaced relative to each other, as in the case of a dislocation.

SUMMARY OF THE INVENTION

These objects, as well as others which will become apparent hereinafter, are achieved by a shoulder prosthesis of the type defined in the foregoing, wherein the anchoring element contains, on the one hand, in its upper part, a stabilizer intended to be introduced into the base of the coracoid process of the scapula and, on the other hand, in its lower part, an orifice for the passage of a fixation means into the spine of the scapula, and wherein the cylindrical rod has a straight cross section substantially equal to that of the housing which constitutes the hollow in the interior of the tubular element.

DESCRIPTION OF PREFERRED EMBODIMENTS

In the present description and in the attached claims, the adjectives "upper", "lower", "horizontal", "vertical", "front" and "rear" are used supposing a subject in vertical position, head up, having the arms in the position which they assume under the effect of gravity alone, observed in facing relationship.

Advantageously, the external wall of the tubular element is flared at its upper end in the form of a truncated cone, the bases of which are substantially perpendicular to the axis of this tubular element, the upper base coinciding with the level of the transverse cut made to remove the head of the humerus; this upper base of the truncated cone is preferably extended, in the direction of the internal face of the humerus; by a flat nose; the lower end of the tubular element is of rounded shape; the straight cross section of the rod and that of the interior housing of the tubular element are circular.

In order to improve the maintenance of this humeral piece in the humerus, it is advantageous for the exterior surface of this tubular element to contain horizontal grooves near the upper end thereof as well as vertical grooves.

Preferably, the tubular element has a length of between 8 and 10 cm, a wall thickness of between 0.15 and 0.25 cm and an outside diameter of between 10 and 14 mm, the truncated cone having a height of 2 to 2.5 cm and the upper base thereof having a diameter of 20 to 30 mm; the interior housing has a depth of between 7 and 9 cm.

The rod, at the side of its upper end, has a disk perpendicular to its axis, disposed at a certain distance from the ball. The distance between the lower end of the rod and the lower face of the disk is at least equal to the depth of the interior housing of the tubular element. The distance between the upper face of the disk, turned toward the ball, and the base of this ball, is advantageously between 12 and 15 mm; the diameter of the ball is between approximately 10 and 15 mm when a glenoid piece is used and is 35 to 50 mm when the socket of the scapula is used.

According to an advantageous embodiment, the anchoring element and the hemispherical element of the glenoid piece are two separate elements joined together by a binding means. Advantageously, the stabilizer of the anchoring element takes an angle of approximately 30° with the vertical in the direction of the front face of the scapula.

According to a preferred embodiment, the anchoring element consists of a solid member, the horizontal cross sections of which are substantially isoceles triangles; the lower part of said solid member has a substantially plane external face which is level with the bone at the position of the socket and supports a projecting rectangular stud provided with retaining means cooperating with the binding means, a fin being provided at the base of said external face in such a manner that it faces the spine of the scapula, said fin containing the orifice for the passage of the fixation means embedded in said spine, the upper part of said solid member forming the bond between said lower part and the stabilizer, the width of said solid member in its external face, measured horizontally, being maximum at the position of the stud and decreasing progressively toward the fin and the stabilizer, a contraction nevertheless being provided between the upper and lower parts, the stabilizer being situated to the rear relative to the external face and being connected thereto by a plane which is oblique relative to the external face. For example, the means cooperating with the binding means can be a tunnel traversing the stud from one side to the other, the binding means then being a pin.

Advantageously, the hemispherical element contains a hemispherical cup in which the ball of the humeral piece is seated, and a receptacle which can cuff the stud of the anchoring element. This hemispherical cup is slightly retentive relative to the ball of the humeral piece. In certain cases, the hemispherical element can contain a plate, which is supported on the internal face of the acromion of the scapula in which the glenoid piece is fixed.

The tubular element and the hemispherical element are advantageously fabricated from a high-density polyethylene, whereas the rod as well as the anchoring element are metallic.

The description which follows and which has no limitative character must be read with reference to the attached figures, in which:

FIG. 7 is a view corresponding to FIG. 1, the glenoid part of the shoulder prosthesis being implanted in the scapula, the initial humerus being represented by dot-dash lines.

FIG. 8 is an exploded perspective view of the two elements of the glenoid piece according to an embodiment of the invention.

FIG. 9 is a side view of the elements shown in FIG. 8.

FIG. 10 is a view according to the line X—X of FIG. 9.

Figure 1:
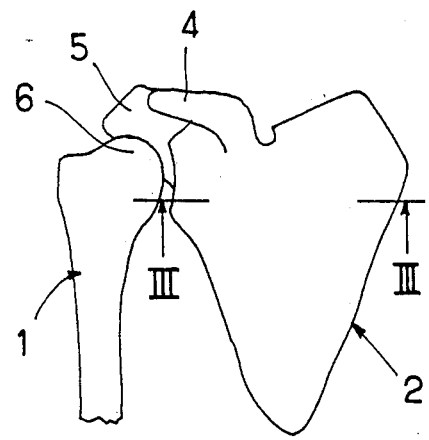
FIG. 1 represents a central view, i.e., a front view, of a scapula and of a humerus, in the present case of the right scapula and humerus.
Figure 5:
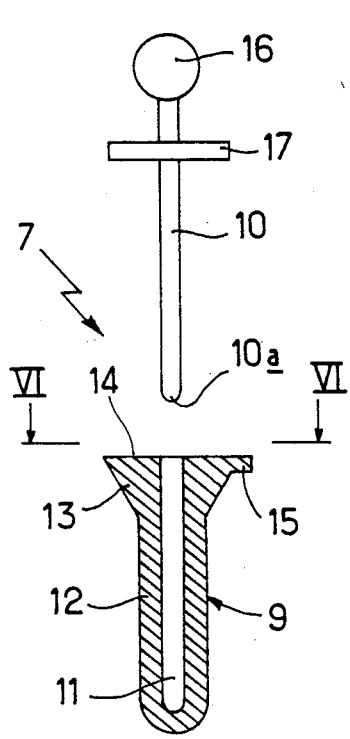
FIG. 5 is an exploded and cross-sectional view of the humeral piece of the shoulder prosthesis of FIG. 4.
Figure 6:
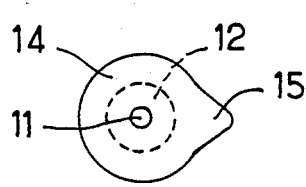
FIG. 6 is an top plan view according to the line VI—VI of FIG. 5.
Figure 2:
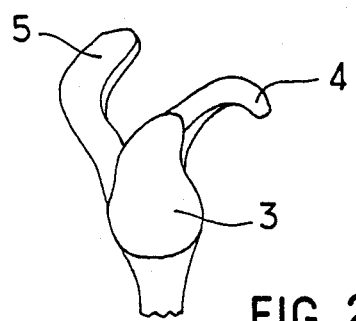
FIG. 2 is a side view of the humeral joint zone of the scapula of FIG. 1.
Figure 3:
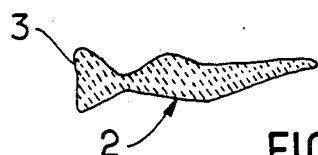
FIG. 3 is a cross-sectional view of the scapula of FIG. 1, according to the line III—III of FIG. 1.

As can be seen in FIGS. 1 to 3, a shoulder is the joint of a humerus 1 with the shoulder girdle and in particular with the scapula 2 of this girdle.

The scapula 2 is a bone substantially triangular shape, one apex of which is directed downward. This bone is relatively flat, as can be seen from FIG. 3: its thickness is approximately 1 cm, which is the source of many problems in introducing a prosthetic element into this thickness. It actually contains two swellings, one named the spine, situated substantially along its side facing the humerus 1, and the other starting from the glenoid cavity 3 and corresponding to the base of the coracoid process 4, which is situated on the front face of the scapula. The glenoid cavity 3 is the cavity which the scapula 2 presents toward the head 6 of the humerus 1. This glenoid cavity 3 has the general shape of a pear, the top of which would be directed toward the coracoid process 4. On the dorsal or rear face of this scapula, and substantially facing the base of the coracoid process 4, there is situated the acromion 5.

Figure 4:
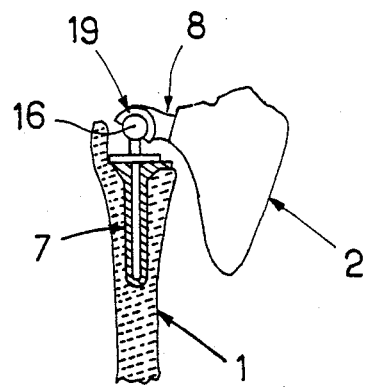
FIG. 4 is a shoulder prosthesis according to the invention after it has been installed, the humerus being cut off.

The shoulder prosthesis according to the present invention, as shown in FIG. 4, comprises a humeral piece 7 and a glenoid piece 8: the humeral piece 7 is implanted in the bone of the humerus 1, along the longitudinal axis of this bone; the glenoid piece 8 is implanted in the glenoid cavity 3 and covers the top of the humeral piece 7, as will be described hereinafter.

The humeral piece 7 comprises a tubular element 9, which is hollow and which is implanted in the bone of the humerus, and a substantially cylindrical solid rod 10. The tubular element 9 therefore comprises a longitudinal housing or channel 11 which is open at its upper part and closed at its lower part. The outer wall 12 of the tubular element is flared at its upper end in the form of a truncated cone 13, the upper base of which is perpendicular to the axis of the tubular element 9 and coincides with the level of the cut made to remove the head of the humerus when it is desired to install the prosthesis (see FIG. 1). Toward the internal face of the humerus 1, the upper base 14 of the truncated cone 13 is extended by a flat nose 15. The rod 10 and the channel 11 have circular cross sections which are equal except for the clearance.

The dimensions of the tubular element 9 are a function of those of the humerus 1. It is considered that it is sufficient to use one of the three models listed in Table I to cover every type of humerus.

Figure 12:
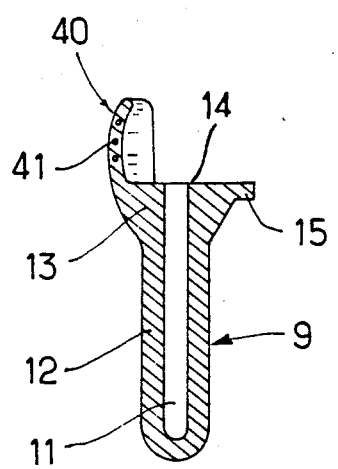
FIG. 12 represents an alternative embodiment of the tubular element of the humeral piece which is the subject matter of FIG. 5.

According to an alternative embodiment, shown in FIG. 12, the tubular element 9 can contain a shield 40 in the form of an arc of a circle disposed at the periphery of the upper base 14 of the truncated cone 13 and opposite the flat nose 15. This shield must be present in particular to attach the muscles, by ligature by means of wires passing into tunnels 41, of which there are two or three, when the corresponding part of the humerus cannot be saved. The tunnels 41 are drilled in the thickness of the shield 40 perpendicular to its radius of curvature. For example, this shield has a height of 3 cm and a width of 3 cm. As regards its curvature, it must be identical to that of the disk 17 of the rod 10 described above.

The other part of the humeral piece, the rod 10, contains at its upper end a ball 16, while its lower end 10a is disposed in the channel 11 of the tubular element 9: this latter and the rod 10 can slide relative to each other.

At a distance from its lower end 10a equal to the length of the interior channel of the tubular element 9, the rod 10 carries a disk 17, which is perpendicular to the axis of said rod. The lower face of this disk 17 can come into contact with the upper base 14 of the truncated cone 13. The thickness of the disk 17, which is normally 2 mm, can vary until 2 cm in such a manner as to compensate for any shortening of the humerus necessary for implantation of the prosthesis according to the invention. The distance between the upper face of the disk 17, i.e., that turned toward the ball 16, and the base of this ball 16 is between 12 and 15 mm depending on the humeral-piece model, as indicated in Table I hereinafter. As regards the diameter of the ball 16, it also depends on the humeral-piece model: it can vary from 15 to 30 mm.

A larger ball can also be provided, because in some cases the scapula is not worn out. It suffices in this case to replace the head 6 of the humerus 1: thus no piece is fixed in the scapula, and consequently the ball 16 must occupy the entire normal volume of the head 6 of the humerus 1. The diameter of such a sphere will therefore have to approximate that of the normal head of the humerus: because of this fact, it will vary between 35 and 50 mm. This ball of larger diameter can also be formed starting from a ball of small diameter, such as described in the foregoing, on which disposed a retentive cup, which is not fixed to the scapula 2. This assembly permits the movements to be partly distributed between the ball and the cup on the one hand and the cup and the scapula on the other hand.

Figure 13:
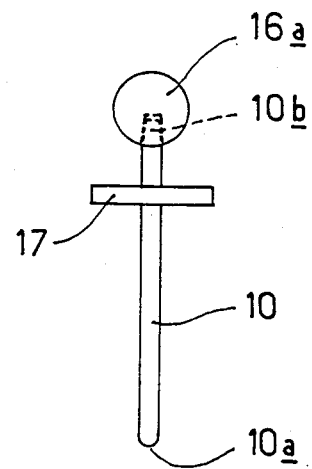
FIG. 13 represents an alternative embodiment of the rod of the humeral piece which is the subject matter of FIG. 5.

According to an alternative embodiment shown in FIG. 13, the rod 10 contains at its upper end a ball 16a which is forcibly fitted onto the end 10b of the rod which is shaped as a truncated cone known as a Morse cone. In this case, the rod 10 can be identical for all the prosthesis models: only the sphere 16a being specific. In this alternative embodiment, the dimensions of the elements of the humeral piece 7 are listed in Table II hereinafter.

As stated in the foregoing, the shoulder prosthesis, depending on the embodiment of the present invention, comprises on the one hand the humeral piece 7 described in the foregoing, and on the other hand the glenoid piece 8. This latter, according to the present practical example, consists of two elements: an anchoring element 18, which is intended to be introduced partly into the scapula at the location of the glenoid cavity 3, and a hemispherical element 19, which cooperates with the ball 16 of the humeral piece 7. The anchoring element 18 and the hemispherical element 19 are joined together by a pin (not shown).

Figure 11:
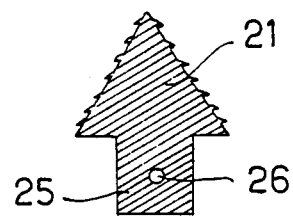
FIG. 11 is a cross section according to the line XI—XI of FIG. 10.

The anchoring element 18 contains, on the one hand, a flat stabilizer 20 and, on the other hand, a solid member 21 having in vertical section substantially the shape of a pear, just as the glenoid cavity 3. This solid member 21, the horizontal sections of which are isoceles triangles, and the walls of which, being intended to penetrate into the scapula, contain horizontal striations, as shown in FIG. 11, comprises an upper part 21a topped by the stabilizer 20 and a lower part 21b containing at its base a fin 31 provided with an orifice 22 for the passage of a screw 23, which constitutes a means of fixation in the spine of the scapula 2. Between the upper 21a and lower 21b parts there exists a contraction 24 on each side of the solid member 21.

The anchoring element 18 also comprises a stud 25 disposed on the external face 30 of the lower part 21b of the solid member 21; this stud is of rectangular shape and contains a vertical tunnel 26 traversing it from one side to the other for the passage of the pin which permits the hemispherical element 19 to be fixed to the anchoring element 18. The broadest zone of the external face 30 is situated at the location of the stud 25, and the solid member 21 has a width, measured from front to rear, which decreases progressively toward the fin 31 and toward the stabilizer 20. The stabilizer 20 is situated to the rear relative to the external face 30, and it is attached thereto by an oblique plane 32. The lower edge of the part 21b is rounded from the external face 30 toward the central zone of the scapula to facilitate the introduction of the prosthesis into the cavity intended therefor.

The hemispherical element 19 contains a cup 27 disposed on a U-shaped receptacle 28, which cuffs the stud 25 of the anchoring element 18. The receptacle 28 also comprises a passage 29, which comes into the extension of the tunnel 26 to permit housing of the pin which ensures the joining together of the two elements of the glenoid piece 8.

The hemispherical cup 27, when the shoulder prosthesis is installed, cuffs the head 16 of the humeral piece 7 and exerts thereon a slight retentive action, since its volume is slightly larger than that of a hemisphere of the same diameter. This slightly retentive character ensures stability in the movements, while permitting the two pieces of the prosthesis to come apart, thus avoiding fracture of the scapula or detachment of these pieces from the bone.

When the glenoid piece 8 is introduced into a scapula 2, the stabilizer 20 becomes situated at the base of the coracoid process 4, while the orifice 22 permits the screw 23 to be introduced into the spine of this scapula 2. This arrangement thus takes advantage of the thickest parts of the scapula. Because of this fact, the stabilizer 20 makes an angle with the vertical of approximately 30° toward the front.

In Table III hereinafter, there are listed the dimensional characteristics of the glenoid piece 8 according to the three most common models which cooperate with the corresponding models of the humeral piece 7.

The tubular element 9 of the humeral piece 7 as well as the hemispherical element 19 of the glenoid piece 8 are fabricated from a high-density polyethylene; the rod 10 of the humeral piece 7 and the anchoring element 18 of the glenoid piece 8 are of stainless steel.

The shoulder prosthesis which has just been described therefore makes it possible, on the one hand, to maintain stability between the two pieces of which it consists while permitting great mobility, as has been stated, and, on the other hand, to reduce the forces acting on the fixation of the different pieces in the corresponding bones, while permitting a rotational movement and a longitudinal movement between the humeral element 9, which is fixed in the humeral 1, and the rod 10 carrying the ball 16. In fact, the rod 10 is movable in the interior of the channel 11 of the humeral element 9, which in turn is fixed in the bone of the humerus 1.

This has the advantage in particular of being able to take charge of the rotational movements and to avoid the occurrence of such movements at the position of the ball 16. The rotational movements are defined in anatomy as being movements which occur arount the longitudinal axis of the arm. These movements are greatly used in everyday living, and are those which favor dislocations of the normal joint. They are also those which are started and stopped by the so-called cuff muscles, which are very often worn out at the shoulder.

This prosthesis also has the advantage of preventing downward loads on the pieces. In fact, the weight of the arm and of the hand tends to pull the humeral piece toward the ground, and, by the intermediary thereof, the piece fixed in the scapula when there exists retentive stability: these loads are prevented, or at least strongly absorbed, by the possibility of sliding of the rod 10 in the humeral element 9.

If the buffer muscles have completely disappeared, a plate supported on the acromion 5 (not shown) is fixed to the hemispherical element 19 of the glenoid piece 8.

TABLE I

|  | Large size | Medium size | Small size |
| --- | --- | --- | --- |
| Tubular element (9) |  |  |  |
| Outside length | 10 cm | 8 cm | 8 cm |
| Length of channel (11) | 9 cm | 7 cm | 7 cm |
| Outside diameter | 12 mm | 10 mm | 10 mm |
| Diameter of channel (11) | 8 mm | 6 mm | 6 mm |
| Height of truncated cone (13) | 2 cm | 3 cm | 2 cm |
| Disk (17) |  |  |  |
| diameter | 30 mm | 25 mm | 20 mm |
| height | 2 mm | 2 mm | 2 mm |
| Rod (10) |  |  |  |
| Length between lower end (10a) and the disk (17) | 9 cm | 7 cm | 7 cm |
| Diameter | 8 mm | 6 mm | 6 mm |
| Ball (16) |  |  |  |
| Diameter | 30 mm | 25 mm | 15 mm |

TABLE II

|  | Large size | Medium size | Small size |
| --- | --- | --- | --- |
| Tubular element (9) |  |  |  |
| . Outside length | 10 cm | 8 cm | 8 cm |
| . Length of channel (11) | 7 cm | 7 cm | 7 cm |
| . Outside diameter | 12 mm | 10 mm | 10 mm |
| . Diameter of channel (11) | 6 mm | 6 mm | 6 mm |
| Height of truncated cone (13) | 2 cm | 2 cm | 2 cm |
| Disk (17) |  |  |  |
| diameter | 20 mm | 20 mm | 20 mm |
| height | 2 mm | 2 mm | 2 mm |
| Rod (10) |  |  |  |
| . Length between lower end (10a) and the disk (17) | 9 cm | 7 cm | 7 cm |
| . Diameter | 6 mm | 6 mm | 6 mm |
| Ball (16) |  |  |  |
| . Diameter | 30 mm | 25 mm | 15 mm |

TABLE III

|  | Large model | Medium model | Small model |
| --- | --- | --- | --- |
| Anchoring element (18) |  |  |  |
| . Height | 35 mm | 30 mm | 30 mm |
| . Width of upper part (21a) | 15 mm | 13 mm | 8 mm |
| . Side length of triangular cross section of the solid member (21) | 20 mm | 15 mm | 10 mm |
| Stabilizer (20) |  |  |  |
| . Length | 10 mm | 10 mm | 10 mm |
| . Width | 10 mm | 10 mm | 10 mm |
| . Thickness | 2 mm[a] 4 mm[b] | 2 mm[a] 4 mm[b] | 2 mm[a] 2 mm[b] |
| Stud (25) |  |  |  |
| . Height | 15 mm | 15 mm | 15 mm |
| . Width | 10 mm | 10 mm | 10 mm |
| . Thickness | 15 mm | 15 mm | 15 mm |

[a] metal
[b] plastic material

I claim:

1. A shoulder prosthesis, comprising a humeral piece (7) intended to be fixed in a humerus (1) to replace at least the head thereof and comprising a hollow tubular element (9) which must be fixed in the humerus (1) substantially along the longitudinal axis thereof and a cylindrical rod (10), the upper end of which carries a ball (16) cooperating with a glenoid bearing surface to form a shoulder joint and the lower end of which is disposed in said tubular element (9), this and the rod (10) being able to slide relative to each other, the glenoid bearing surface consisting of a glenoid piece (8) which comprises an anchoring element intended to be inserted into a cavity formed in the scapula (2) and a female hemispherical element (19), this latter cooperating with the male ball (16) of the humeral piece (7), wherein the anchoring element (18) contains, on the one hand, in its upper part, a stabilizer (20) intended to be introduced into the base of the coracoid process (4) of the scapula (2) and, on the other hand, in its lower part, an orifice (22) for the passage of a fixation means (23) into the spine of the scapula (2), and wherein the cylindrical rod (10) has a straight cross section substantially equal to that of the housing (11) which constitutes the hollow in the interior of the tubular element (9), said anchoring element (18) further comprising a solid member (21), having an upper part (21a) and a lower part (21b), the horizontal cross sections of which are substantially isosceles triangles.

2. The shoulder prosthesis according to claim 1, wherein the external wall (12) of the tubular element (7) is flared at its upper end in the form of a truncated cone (13), the bases of which are substantially perpendicular to the axis of said tubular element (7), the upper base (14) coinciding with the level of the transverse cut made to remove the head (6) of the humerus (1).

3. The shoulder prosthesis according to claim 2, wherein the upper base (14) of the truncated cone (13) is extended, in the direction of the internal face of the humerus (1), by a flat nose (15).

4. The shoulder prosthesis according to claim 1, wherein the lower end of the tubular element (9) is of rounded shape.

5. The shoulder prosthesis according to claim 1, wherein the straight cross section of the rod (10) and that of the interior housing (11) of the tubular element (9) are circular.

6. The shoulder prosthesis according to claim 1, wherein the exterior surface of the tubular element (9) contains horizontal grooves near the upper end thereof as well as vertical grooves.

7. The shoulder prosthesis according to claim 2, wherein the tubular element (7) has a length of between 8 and 10 cm, a wall (12) thickness of between 0.15 and 0.25 cm and an outside diameter of between 10 and 12 mm, wherein the truncated cone (13) has a height of 2 to 2.5 cm and the upper base (14) thereof a diameter of 20 to 30 mm, and wherein the interior housing (11) has a depth of between 7 and 9 cm.

8. The shoulder prosthesis according to claim 1, wherein the rod (10), at the side of its upper end, has a disk (17) perpendicular to its axis, disposed at a certain distance from the ball (16).

9. The shoulder prosthesis according to claim 8, wherein the distance between the lower end (10a) of the rod (10) and the lower face of the disk (17) is at least equal to the depth of the interior housing (11) of the tubular element (9).

10. The shoulder prosthesis according to claim 8, wherein the distance between the upper face of the disk (17), turned toward the ball (16), and the base of said ball (16), is between 12 and 15 mm.

11. The shoulder prosthesis according to claim 1, wherein the diameter of the ball (16) is between approximately 10 and 15 mm.

12. The shoulder prosthesis according to claim 1, wherein the anchoring element (18) and the hemispherical element (19) are two separate elements joined together by a binding means.

13. The shoulder prosthesis according to claim 1, wherein the stabilizer (20) makes an angle of approximately 30° with the vertical in the direction of the front face of the scapula (2).

14. The shoulder prosthesis according to claim 1, wherein the fixation means is a screw (23).

15. The shoulder prosthesis according to claim 12, wherein the lower part (21b) of said solid member (21) has a substantially plane external face (30) which is level with the bone at the position of the socket and supports a projecting rectangular stud (25) provided with retaining means (26) cooperating with the binding means, a fin (31) being provided at the base of said external face (30) in such a manner that it faces the spine of the scapula (2), said fin (31) containing the orifice (22) of the passage of the fixation means (23) embedded in the said spine, the upper part (21a) of said solid member (21) forming the bond between said lower part (21b) and the stabilizer (20), the width of said solid member (21) in its external face, measured horizontally, being maximum at the position of the stud (25) and decreasing progressively toward the fin (31) and the stabilizer (20), a contraction (24) nevertheless being provided between the upper (21a) and lower (21b) parts, the stabilizer (20) being situated to the rear relative to the external face (30) and being connected thereto by a plane (32) which is oblique relative to said external face.

16. The shoulder prosthesis according to claim 15, wherein the means cooperating with the binding means is a vertical tunnel (26) traversing the stud (25) from one side to the other, the binding means being a pin.

17. The shoulder prosthesis according to claim 15, wherein the hemispherical element (19) contains a hemispherical cup (27), in which the ball (16) of the humerical piece (7) is seated, and a receptacle (28) which can cuff the stud (25) of the anchoring element (18).

18. The shoulder prosthesis according to claim 13, wherein the hemispherical element is slightly retentive relative to the ball (16) of the humeral piece (7).

* * * * *